United States Patent [19]

Riblet

[11] Patent Number: 5,257,766
[45] Date of Patent: Nov. 2, 1993

[54] DEVELOPED BLANK LAYOUT ANGLE BRACKET

[76] Inventor: Henry Riblet, 79388 Montego Bay Dr., Bermuda Dunes, Calif. 92201

[21] Appl. No.: 791,976

[22] Filed: Nov. 13, 1991

[51] Int. Cl.$^5$ .............................................. A47G 29/02
[52] U.S. Cl. ........................................ 248/248; 108/108; 211/90
[58] Field of Search ............... 248/248, 247, 300, 245; 211/135, 193, 90; 108/108, 152

[56] References Cited

U.S. PATENT DOCUMENTS

| 624,723 | 5/1899 | Allis . | |
| 698,945 | 4/1902 | Henry . | |
| 921,704 | 5/1909 | Hubbard . | |
| 1,083,763 | 6/1914 | Smedberg . | |
| 1,121,513 | 12/1914 | Lench . | |
| 2,119,500 | 5/1938 | Quigan | 113/116 |
| 2,244,374 | 6/1941 | Riblet | 304/10 |
| 2,321,916 | 11/1941 | Ingerman | 304/32 |
| 2,342,427 | 2/1944 | Riblet | 304/30 |
| 2,376,966 | 5/1945 | Ingerman | 304/32 |
| 2,429,586 | 10/1945 | Rompre | 248/248 |
| 2,854,291 | 9/1958 | Riblet | 304/10 |
| 2,854,293 | 9/1958 | Riblet | 304/30 |
| 3,041,033 | 6/1962 | Schwartz | 248/248 |
| 3,473,774 | 10/1969 | Riblet | 248/246 |
| 3,493,202 | 2/1970 | Jensen | 248/42 |
| 3,698,680 | 10/1972 | Shoemaker | 249/189 |
| 3,854,248 | 12/1974 | Dayus | 49/504 |
| 3,970,277 | 7/1976 | Riblet | 248/246 |
| 4,015,687 | 4/1977 | Dean | 182/220 |
| 4,103,856 | 8/1978 | Riblet | 248/246 |
| 4,360,181 | 11/1982 | Burkholder | 248/248 |
| 4,756,430 | 7/1988 | Spamer | 211/135 X |
| 4,895,331 | 1/1990 | Nehls | 248/245 |
| 4,897,979 | 2/1990 | Colonias | 56/643 |

FOREIGN PATENT DOCUMENTS

| 2364415 | 7/1975 | Fed. Rep. of Germany | 248/248 |
| 160396 | 3/1933 | Switzerland | 248/248 |
| 566891 | 1/1945 | United Kingdom | 248/247 |
| 638239 | 12/1947 | United Kingdom | 248/248 |

Primary Examiner—J. Franklin Foss
Attorney, Agent, or Firm—Wolf, Greenfield & Sacks

[57] ABSTRACT

An angle bracket constructed from a single piece metal blank. The bracket is of a substantially triangular shape. In one embodiment of the invention the bracket has a U-shaped cross-section providing added stability. A method is disclosed for constructing the bracket from the metal blank. The method includes the steps of folding the metal blank along preformed fold lines to form its triangular shape. The method also includes the steps of folding the metal blank along additional preformed fold lines to form its U-shaped cross-section.

43 Claims, 4 Drawing Sheets

DEVELOPED BLANK LAYOUT ANGLE BRACKET

BACKGROUND OF THE INVENTION

1. Field of the Invention

This invention relates in general to an angle bracket for use in supporting various structures. More particularly, this invention pertains to an improved angle bracket of simple construction.

2. Background Discussion

Brackets are utilized in a number of applications to support various structures. For example, angled brackets are often utilized to support planks to form a shelf or scaffold structure. Reference is made herein to U.S. Pat. Nos. 3,970,277, 3,473,774 and 4,103,856, each relating to brackets for supporting scaffold structures. Although the brackets disclosed in these patents function quite satisfactorily, they each employ a plurality of components. Each of these prior art brackets utilizes a plurality of main structural components and a plurality of connecting parts such as nuts, bolts, rods and pins to interconnect the main structural components. Because of the plurality of parts involved, these prior art brackets are somewhat costly to manufacture and somewhat difficult to assemble.

Accordingly, it is an object of the present invention to provide an angle bracket that functions as well or better than known prior art brackets but is less costly and simpler to construct.

It is a further object of the present invention to develop a method for constructing a simpler and less costly angle bracket.

SUMMARY OF THE INVENTION

To accomplish the foregoing and other objects, features and advantages of the invention, there is provided a single piece angle bracket constructed from a metal blank. In one embodiment of the invention, the angle bracket has a substantially U-shaped cross section supplying added support and stability.

There is further provided a method for constructing a single piece angle bracket from a metal blank. The method includes the steps of establishing transverse fold lines in the blank, folding the blank along the transverse fold lines to form a substantially triangular shape and interconnecting opposite ends of the blank so that the blank maintains its triangular shape.

The present invention further provides a method for constructing a single piece scaffold bracket with a substantially U-shaped cross section. The method includes the steps of establishing longitudinal fold lines in the blank and folding the blank along the longitudinal fold lines to form a substantially U-shaped cross section.

BRIEF DESCRIPTION OF THE DRAWINGS

Numerous other objects, features and advantages of the invention should now become apparent upon a reading of the following detailed description taken in conjunction with the accompanying drawings, in which.

DETAILED DESCRIPTION

Figures 1, 2, 3, 4:
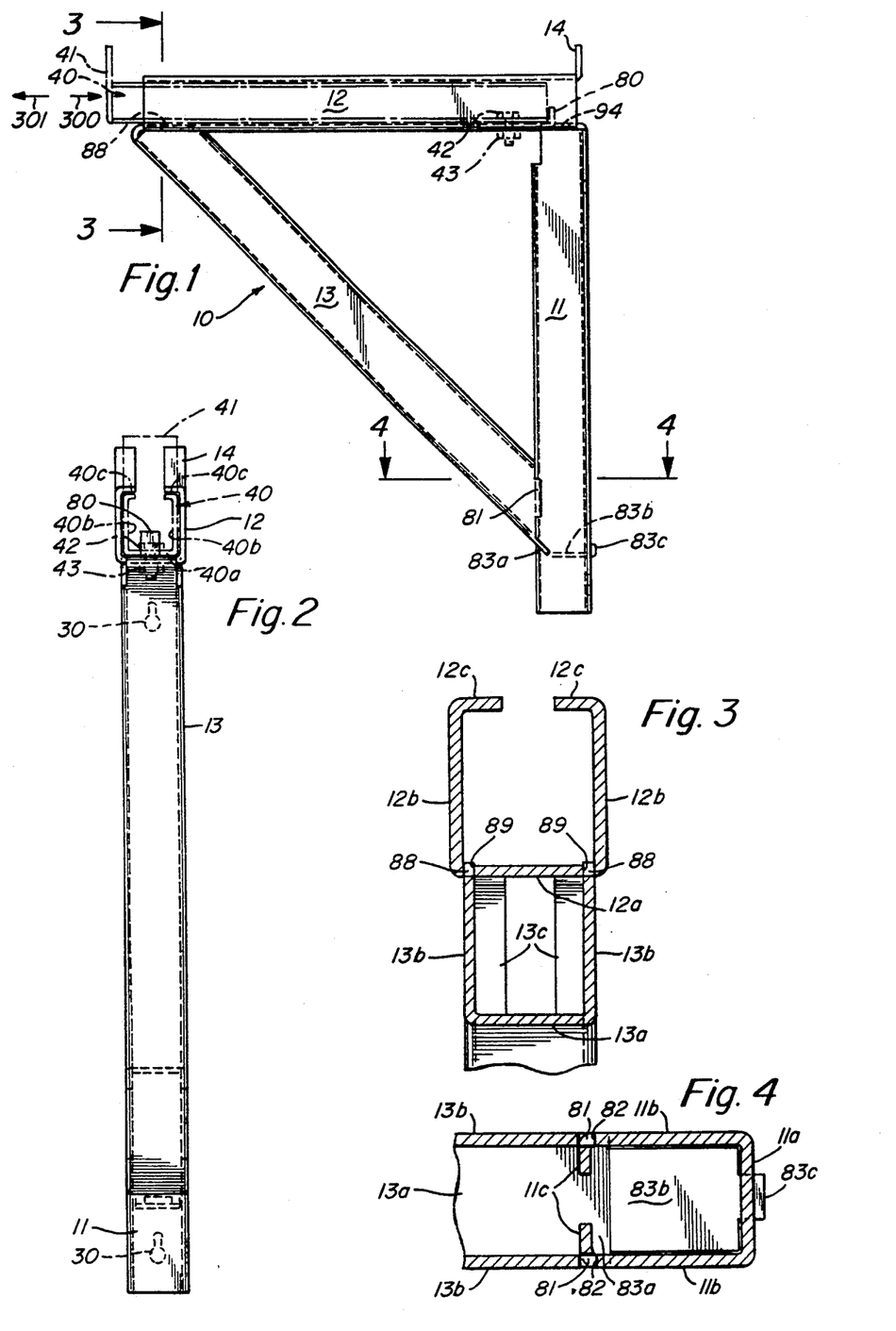
FIG. 1 is a side elevation view of the preferred embodiment bracket.
FIG. 2 is an end view of the preferred embodiment bracket.
FIG. 3 is a cross sectional view of the bracket taken along line 3—3 of FIG. 1.
FIG. 4 is a cross section view taken along line 4—4 of FIG. 1 illustrating the attachment of the vertical and cross legs of the angle bracket.

FIG. 1 is a side elevational view of the bracket 10. The bracket 10 has a substantially triangular shape created by a vertical leg 11, a horizontal leg 12 and a cross leg 13. Various alignment and locking tabs fit within corresponding slots at the respective intersections of the legs, thereby providing stability to the bracket 10 and ensuring that it maintains its triangular shape. The tabs and slots are described in detail later in this specification.

It should be understood that, depending upon the application in which it is used, the bracket 10 can be connected to a number of varying surfaces. For example, a pair of brackets can be attached to a flat wall surface and be used to support a horizontal plank in order to form a shelf. For this application, the vertical leg 11 is provided with upper and lower keyslots 30 which are shown most clearly in FIG. 2. The keyslots 30 can accommodate screws, nails or the like extending out from the wall surface and thereby enable the bracket to be attached to the wall surface. Alternatively, a pair of brackets can each be connected to an upright post and be adjustably locked into position at a given height along the upright post. In this manner, the brackets can be utilized to support a plank that can be used to form a scaffold. The adjustable connection to the upright post can be accomplished through a number of different ways known to those skilled in the art. As shown in FIG. 1, the bracket 10 is connected to a bracket extension 40. The extension 40 can be slid in the direction of arrow 301 to enable the bracket 10 to support a wide platform. The extension 40 is connected to the bracket 10 by a bolt 42 and a nut 43.

A potential problem with using a shelf or scaffold comprised of a platform supported by brackets, is that the platform could potentially slide off of the brackets. A slippage of the platform off of the brackets could result in damage to any items stored on a shelf or personal injury to any workmen working on a scaffold. To address this potential problem, platform stops 14 and 41 may be provided, respectively extending normally from horizontal leg 12 and extension 40. If the platform begins to slide in either direction, the platform will contact one of the platform stops which will prevent it from sliding off of the bracket 10.

FIG. 2 shows the U-shaped cross sections of the horizontal leg 12 and extension 40. The cross leg 13 and vertical leg 11 similarly have a U-shaped cross-sections as illustrated, for example, in FIG. 7. Vertical leg 11, horizontal leg 12 and cross leg 13 respectively have sidewalls 11b, 12b and 13b as well as flanges 11c, 12c and 13c. Similarly, extension 40 has sidewalls 40b and flanges 40c. The extension 40 may be constructed from a metal blank in a manner similar to the construction of the bracket 10. The extension 40 has a similar U-shaped cross section and is of slightly smaller dimensions than the bracket 10. The smaller dimensions allow the extension 40 to telescope inside the U-shaped channel of horizontal leg 12. The extension can be slid, as illustrated in FIG. 1, in the direction of arrow 300 when a narrow platform is used so that the extension 40 will fit substantially within the horizontal leg 12. The extension 40 can also slide in the direction of arrow 301 to provide the bracket with the capability of supporting a wide platform. Plank stops 14 extend normally from the inward facing flanges 12c of the vertical leg 12. Plank stop 41 extends normally from the base 40a of extension 40.

Reference is again made to FIG. 1 which shows connections of various portions of the bracket in phantom. For example, the connections between extension 40 and horizontal leg 12 are shown in phantom. Extension 40 telescopes inside the channel created by the U-shaped cross-section of horizontal leg 12. Extension 40 lies above the base 12a and below the flanges 12c of the horizontal leg 12. The extension 40 is connected to the base 12a of the horizontal leg 12 via a bolt 42 and nut 43. In one embodiment of the invention not shown, the base 12a of the horizontal leg 12 can be provided with a slot running along its length and allowing the bolt 42 to pass through the horizontal leg 12. The slot allows the extension 40 and the bolt to slide in relation to the horizontal leg 12. When the extension 40 is slid into the desired position, the nut 43 can be tightened to secure the extension 40 into position. In another embodiment of the invention, also not shown, the horizontal leg 12 is provided with several spaced holes for accommodating the bolt 42 and for allowing the extension 40 to be locked into various extended positions relative to the horizontal leg 12. In FIG. 1, the extension 40 is not in its extended position. In this non extended position, the extension 40 contacts an extension stop 80 that extends from the base 12a of the horizontal leg 12. The extension stop 80 prevents the extension 40 from being inserted any further into the horizontal leg 12 in the direction shown by arrow 300. One platform stop 14 is shown extending normally from one inward facing flange 12c.

FIG. 1 also shows the connections between the horizontal leg 12 and the vertical leg 11 in phantom. Alignment tabs 94 extend from the sidewalls 11b of the vertical leg 11 and fit through slots 95 within the base 12a of the horizontal leg 12. The slots 95 are shown for example in FIG. 5.

FIG. 4 also illustrates the connections between the vertical leg 11 and the cross leg 13 in phantom. Alignment tabs 81 extend from the side walls 13b of the cross leg 13 and fit into slots 82 in the flanges 11c of the vertical leg 11. Alignment tabs 81 are stepped inward slightly from the side walls 13b to allow for the proper alignment with slots 82. Slots 82 are shown for example in FIG. 5. A locking tab 83 extends from the base 13c of the cross leg 13. The locking tab 83 passes through slots 84 that are established in the flanges 11c and upstanding walls 11b of the vertical leg 11, and also fits within a locking slot 85 provided in the base 11a of the vertical leg 11. Slots 84 and 85 are shown for example in FIG. 5.

Locking tab 83 consists of three portions: cross portion 83a fits within the slot 84; horizontal portion 83b extends through the U-shaped channel of the vertical leg 11; and vertical portion 83c fits through locking slot 85 and is folded upward to contact the outer surface of the base 11a of the vertical leg 11. The contact between the vertical portion 83c of the locking tab and the outer surface of the base 11a of the vertical leg 11 prevents the cross leg 13 from disengaging from the vertical leg 11 and ensures that the bracket 10 maintains its triangular shape.

Finally, FIG. 1 shows the connection between the horizontal leg 12 and the cross leg 13 in phantom. Alignment tabs 88 extend from the upstanding walls 13b of the cross leg 13 and fit into slots 89 in the base 12a of the horizontal leg 12. The slots 89 are shown for example in FIG. 5

FIG. 2 is a cross sectional view of the bracket. This view shows the extension 40 telescoped inside the U-shape cross-section of horizontal leg 12. This view also shows bolt 42 that attaches the extension 40 to the horizontal leg 12. The extension stop 80 is shown as extending from the base 12a of the vertical leg 12. The extension stop 80 is folded out of the base 12a and leaves an opening 93 in the base 12a as shown for example in FIG. 6.

FIG. 3 is a cross sectional view taken along line 3—3 shown in FIG. 1 but without showing the extension 40. The U-shaped cross section of horizontal leg 12 is shown. Alignment tabs 88 extend from the upstanding walls 13b of the cross leg and into slots 89 within the base 12a of the horizontal leg 12. Slots 89 are shown for example in FIG. 5. The bottom surface of flanges 13c of cross leg 13 are shown Also, the bottom surface of the base 13a of cross leg 13 is shown extending downward away from line 3—3 as shown in FIG. 1.

FIG. 4 shows a cross sectional view taken along line 4—4 shown in FIG. 1. This view shows the connection between the vertical leg 11 and the cross leg 13. Alignment tabs 81 extend from the side walls 13b of the cross leg 13 and fit into slots 82 in the flanges 11c of the vertical leg 11. As a result, the flange 11c is shown extending underneath the alignment tab 81. The locking tab 83 is shown extending from the base 13c of the cross leg 13. Cross portion 83a of the locking tab fits within the slots 84 that are provided in the flanges 11c and upstanding walls 11b of the vertical leg 11 and thereby extends slightly into the U-shaped channel defined in the vertical leg 11. Horizontal portion 83b of the locking tab extends across the U-shaped channel to the base 11a . Vertical portion 83c of the locking tab 83 fits through locking slot 85 and is folded upward to contact the outer surface of the base 11a of the vertical leg 11. The contact between the vertical portion 83c of the locking tab and the outer surface of the base 11a of the vertical leg 11 prevents the cross leg 13 from disengaging from the vertical leg 11 and ensures that the bracket 10 maintains its triangular shape.

Figure 5:
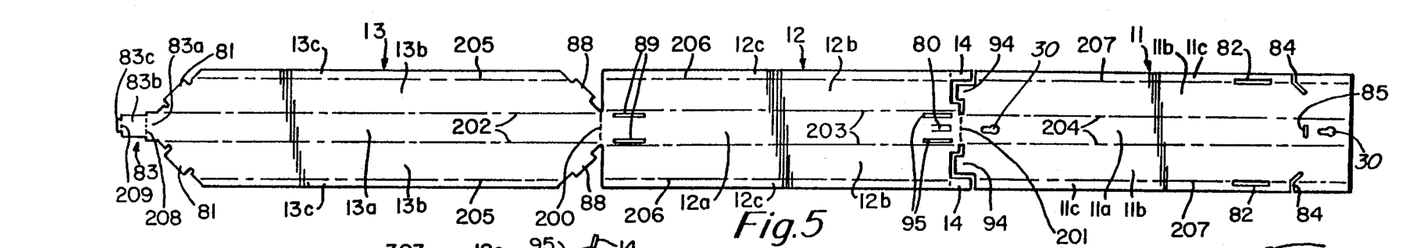
FIG. 5 is a plan view of the metal blank.
Figure 6:
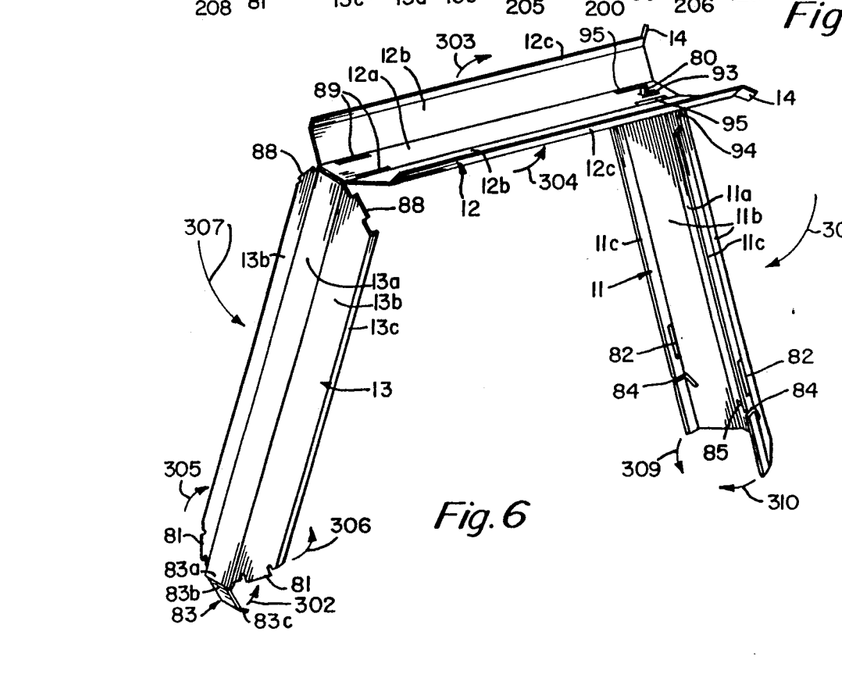
FIG. 6 is a perspective view of the metal blank being folded.

FIG. 5 shows a top plan view of the metal blank used to form the bracket of the present invention. This view shows each of the tabs, slots and holes previously discussed. Transverse fold lines 200 and 201 extend transversely with respect to the length of the blank. These transverse fold lines allow for the folding of the metal blank as will be described later in this specification. Inner longitudinal fold lines 202, 203 and 204 extend respectively along the lengths of cross leg 13, horizontal leg 12 and vertical leg 11. Inner fold lines 203 are slightly wider than inner fold lines 202 and 204. The greater width of the inner fold lines along the horizontal leg 12 allow for proper alignment of alignment tabs 88 with slots 89, as shown in FIG. 6, and for proper alignment of tabs 94 with slots 95, as shown in FIG. 5. Outer longitudinal fold lines 205, 206 and 207 also extend respectively along the lengths of cross leg 13, horizontal leg 12 and vertical leg 11. The inner and outer longitudinal fold lines also allow for folding of the metal blank as will be described below.

FIG. 6 shows the metal blank undergoing folding to form the triangular angle bracket 10. Although this folding operation is described herein in a certain sequence, the folding operations need not be performed in any particular order. Vertical leg 11 is folded along transverse fold line 201 in the direction of arrow 308. The folding will continue in the direction of arrow 308 until the angle between the horizontal leg 12 and the vertical leg 11 is approximately 90 degrees. Cross leg 13 is folded inward in the direction of arrow 307 along transverse fold line 200 until the angle between the cross leg 13 and horizontal leg 12 is approximately 45 degrees as shown for example in FIG. 1. Locking tab 83 is folded along transverse fold lines 208 and 209 in the direction of arrow 302.

Figure 7:
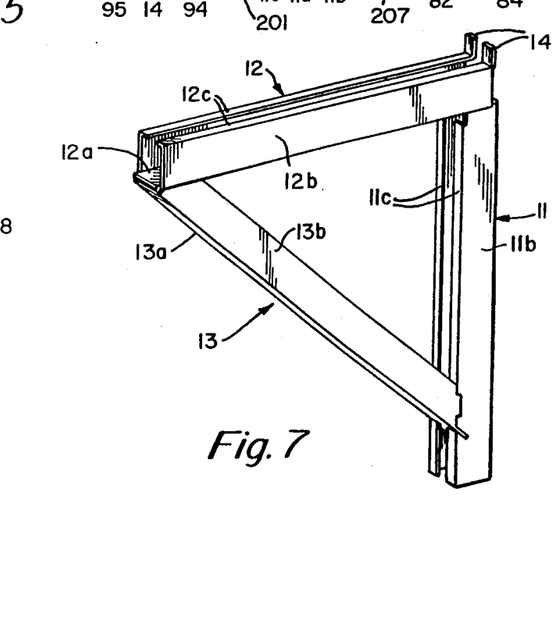
FIG. 7 is a perspective view of the preferred embodiment of the metal blank completely folded to form an angle bracket.

Horizontal leg 12 is folded inward along longitudinal fold lines 203 in the direction of arrows 303 and 304 until the sidewalls 12b extend substantially perpendicular from the base 12a as shown for example in FIG. 7. Similarly, cross leg 13 is folded along longitudinal fold lines 202 in the direction of arrows 305 and 306 until sidewalls 13b extend substantially perpendicular from base 13a and vertical leg 11 is folded along longitudinal fold lines 204 in the direction of arrows 309 and 310 until sidewalls 11b extend substantially perpendicular from base 11a. This folding operation along the longitudinal fold lines provides vertical leg 11, horizontal leg 12 and cross leg 13 with U-shaped cross-sections.

Folding may also be done along longitudinal fold lines 205, 206 and 207. However, in one embodiment of the invention not shown, no folding is done along these longitudinal fold lines. In the preferred embodiment, horizontal leg 12 is folded inward along longitudinal fold lines 206 in the direction of arrows 303 and 304 until the flanges 12c extend substantially perpendicular from the sidewalls 12b as shown for example in FIG. 7. Similarly, cross leg 13 is folded along longitudinal fold lines 205 in the direction of arrows 305 and 306 until flanges 13c extend substantially perpendicular from sidewalls 13b and vertical leg 11 is folded along longitudinal fold lines 207 in the direction of arrows 309 and 310 until flanges 13c extend substantially perpendicular from sidewalls 13b. As a result of this folding, the flanges 11c, 12c and 13c all extend inward toward the center of their respective legs, as shown in FIG. 7, rather than outward and away from the center. In an alternate embodiment of the invention shown in FIG. 8, the flanges 11d, 12d and 13d are respectively folded along longitudinal fold lines 207, 206 and 205 outward away from the centers of their respective legs.

At the intersection of horizontal leg 12 and cross leg 13, alignment tabs 88 are inserted through slots 89. At the intersection of horizontal leg 12 and vertical leg 11, alignment tabs 94 are inserted through slots 95. At the intersection of cross leg 13 and vertical leg 11, locking tab 83 is placed through slots 84 and 85 and alignment tabs 81 are inserted through slots 82.

Figure 8:
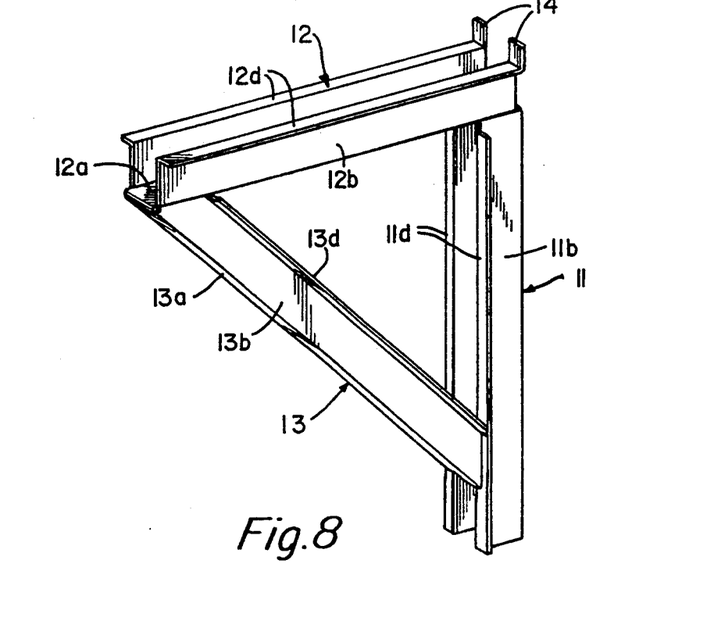
FIG. 8 shows the metal blank folded in an alternate manner to form an alternate embodiment angle bracket.

Platform stops 14 are folded upward from the surface of the flanges 12c and 12d of the horizontal leg 12 such that they are perpendicular to the surface of the flanges 12c and 12d as shown for example in FIGS. 7 and 8. Extension stop 80 is folded upward out of the base 12a of the horizontal leg 12 such that it is perpendicular to the base 12a as shown in FIG. 9.

FIG. 7 is a perspective view of the preferred embodiment of the invention with the metal blank completely folded and the flanges bent inwardly. In the preferred embodiment, the flanges face inwardly because the bracket is therefore more compact and there are no edges extending that, when the bracket is utilized to support a scaffold platform, might interfere with workmen by possibly snagging their clothing.

FIG. 8 is a perspective view of an alternate embodiment of the present invention. Similar components are numbered in the same manner as the embodiment shown in FIG. 7. In this embodiment, flanges 11d, 12d and 13d extend respectively outward from the sidewalls 11b, 12b and 13b of the vertical leg 11, the horizontal leg 12 and the cross leg 13.

Figure 9:
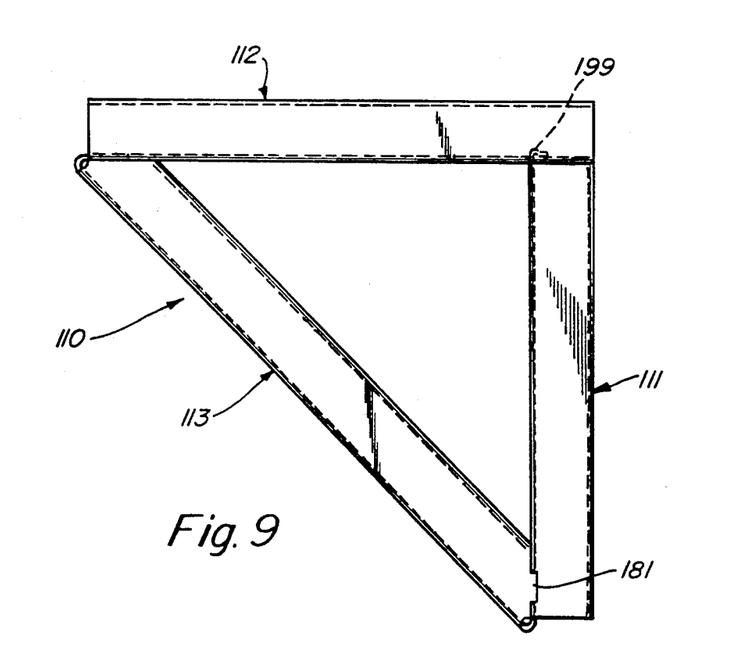
FIG. 9 is a side elevation view of an alternate embodiment of the invention.

FIG. 9 is a side view of an alternate embodiment of the invention. In this embodiment, transverse fold lines are formed at the intersections of the cross leg 113 with both the vertical leg 111 and the horizontal leg 112. Each leg has a U-shaped cross section as is shown more particularly in FIGS. 11-12. The U-shaped cross section of the vertical, horizontal and cross legs are respectively formed by sidewalls 111b, 112b and 113b. The sidewalls 113b of the cross leg 113 extend toward the center of the triangle when the bracket is completely formed. Conversely, the sidewalls 111b and 112b of the vertical leg 111 and horizontal leg 112 extend outward away from the center of the triangle. The interconnections between the vertical, horizontal and cross legs are more fully explained below with reference to FIGS. 10-12.

Figure 10:
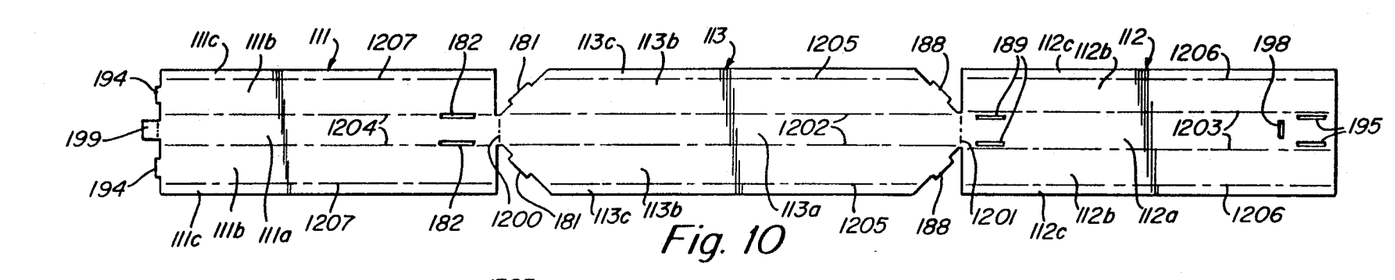
FIG. 10 is a plan view of the metal blank.

FIG. 10 is a top plan view of the metal blank used to form the alternate embodiment of the present invention. Transverse fold lines 1200 and 1201 extend transversely with respect to the length of the blank. These transverse fold lines allow for the folding of the metal blank as will be discussed below. Inner longitudinal fold lines 1202, 1203 and 1204 extend respectively along the lengths of cross leg 113, horizontal leg 112 and vertical leg 111. Inner fold lines 1203 are slightly wider than inner fold lines 1202 and 1204. Greater width of the inner fold lines along the horizontal leg 112 allows for proper alignment of the alignment tabs and slots as is more fully described below. Outer longitudinal fold lines 1205, 1206 and 1207 also extend respectively along the lengths of cross leg 113, horizontal leg 112 and vertical leg 111. The longitudinal and transverse fold lines allow for folding the metal blank as is more fully described below.

FIG. 10 also illustrates the alignment slots and tabs that are utilized to interlock the legs of the bracket and provide support thereto. Alignment tabs 181 extend from the sidewalls 113b of the cross leg 113 and fit into slots 182 in the base 111a of the vertical leg 111. Similarly, alignment tabs 188 extend from the sidewalls 113b of the cross leg 113 and fit into slots 189 in the base 112a of the horizontal leg 112. Additionally, the alignment slots 194 extend from the sidewalls 111b of the vertical leg 111 and fit within the slots 195 in the base 112a of the horizontal leg 112. The locking together of the vertical leg 111 and horizontal leg 112 is accomplished in the following manner. A locking tab 199 extends from the base 11a of the vertical leg 111 and fits through a locking slot 198. Thereafter, the locking tab 199 is bent downward to engage with the surface 112a of the horizontal leg as is shown in FIG. 9. In this manner, the legs are locked together to ensure that the bracket maintains its triangular shape.

Figure 11:
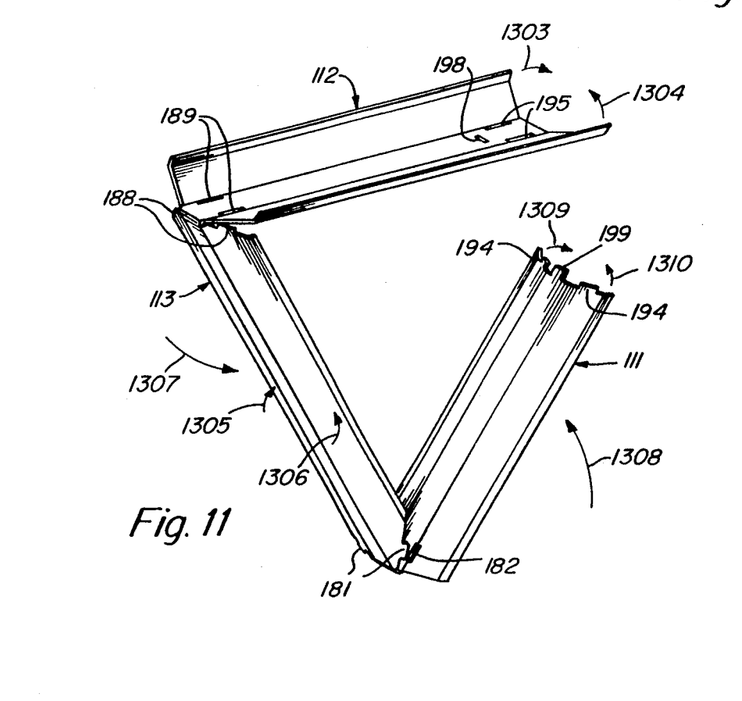
FIG. 11 is a perspective view of the metal bland being folded.

FIG. 11 shows the metal blank undergoing folding to form the alternate embodiment triangular angle bracket 110 shown in FIG. 9. Although this folding operation is described herein in a certain sequence, the folding operations need not be performed in any particular order. Vertical leg 111 is folded along transverse fold line 1200 in the direction of arrow 1308. The folding will continue in the direction of 1308 until the angle between the vertical leg 111 and the cross leg 113 is approximately 45°. Cross leg 113 is folded inward in the direction of arrow 1307 along transverse fold line 1201 until the angle between the cross leg 113 and horizontal leg 112 is approximately 45° as shown for example in FIG. 9.

Figure 12:
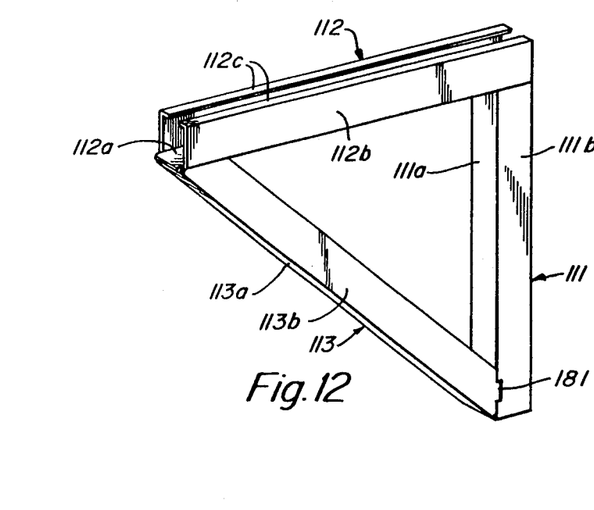
FIG. 12 is a perspective view of the preferred embodiment of the metal blank completely folded to form an angle bracket.

Horizontal leg 112 is folded inward along longitudinal fold lines 1203 in the direction of arrows 1303 and 1304 until the sidewalls 112b extend substantially perpendicular from the base 112a as shown for example in FIG. 12. Similarly, cross leg 113 is folded along longitudinal fold lines 1202 in the direction of arrows 1305 and 1306 until sidewalls 113b extend substantially perpendicular from base 113a and vertical leg 111 is folded along longitudinal fold lines 1204 in the direction of arrows 1309 and 1310 until sidewalls 111b extend substantially perpendicular from base 111a. This folding operation along longitudinal fold lines provides vertical leg 111, horizontal leg 112 and cross leg 113 with U-shaped cross sections.

Folding may also be done along longitudinal fold lines 1205, 1206 and 1207. However, in one embodiment of the invention not shown, no folding is done along these longitudinal fold lines. In the preferred alternate embodiment, horizontal leg 112 is folded inward along longitudinal fold lines 1206 in the direction of arrows 1303 and 1304 until the flanges 112c extend substantially perpendicular from the sidewalls 112b as shown for example in FIG. 12. Similarly, cross leg 113 is folded along longitudinal fold lines 1205 in the direction of arrows 1305 and 1306 until flanges 113c extend substantially perpendicular from sidewalls 113b and vertical leg 111 is folded along longitudinal fold lines 1207 in the direction of arrows 1309 and 1310 until flanges 113c extend substantially perpendicular from sidewalls 113b. As a result of this folding, flanges 111c, 112c and 113c all extend inward toward the center of their respective legs, as shown in FIG. 12, rather than outward and away from the center. In an alternate embodiment of the invention not shown, the flanges are folded along longitudinal fold lines 1205, 1206 and 1207 outward away from the centers of their respective legs.

As the folding continues, the alignment tabs 181, 188 and 194 are respectfully inserted into alignment slots 182, 189 and 195. At the intersection of the horizontal leg 112 and vertical leg 111, locking tab 199 is inserted through locking slot 198 and bent downward so as to lock the bracket into its triangular position.

FIG. 12 is a perspective view of the alternate embodiment of the invention with the metal blank completely folded and the flanges bent inwardly. In this embodiment, the flanges face inwardly because the bracket is therefore more compact and there are no edges extending that, if the bracket is utilized to support a scaffold platform, might interfere with workmen by possibly snagging their clothing.

It will be apparent to those skilled in the art that various modifications and variations can be made in the embodiments of the invention described herein without departing from the scope and spirit of the invention. Such embodiments of the invention will be apparent to those skilled in the art from consideration of the specification and the practice of the invention disclosed herein. It is intended that the specification and embodiments described herein be considered as examples only and that the true scope and spirit of the invention be defined by the following claims.

What is claimed is:

1. An angle bracket formed from a single piece metal blank, the angle bracket comprising:

first, second and third legs, the first leg being contiguous with the second leg, the second leg being contiguous with the third leg, said legs, being positioned to define a substantially triangular bracket;

the first leg having a tab and the third leg having a slot, the tab being interlocked with the slot to interconnect the first and third legs.

2. An angle bracket as claimed in claim 1 further comprising:

strengthening means for strengthening an interconnection between said first and second legs.

3. An angle bracket as claimed in claim 2 wherein said strengthening means includes at least one tab extending from said first leg and at least one slot within the second leg for receiving said tab.

4. An angle bracket as claimed in claim 2 wherein said strengthening means includes at least one tab extending from said second leg and at least one slot within the first leg for receiving said tab.

5. An angle bracket as defined in claim 1 wherein said first second and third legs each have a substantially U-shaped cross-section.

6. An angle bracket as defined in claim 5 wherein each leg has a width and wherein the angle bracket further includes:

a base extending substantially across the width of each leg, the base having first and second sides; and upstanding sidewalls extending from the first and second sides of the base along each leg to form the substantially U-shaped cross-section.

7. An angle bracket formed from a single piece metal blank, the angle bracket comprising:

first, second and third legs, the first leg being contiguous with the second leg, the second leg being contiguous with the third leg, said legs being positioned to define a substantially triangular bracket, said first and third legs having means for defining an interconnection between said first and third legs;

said first, second and third legs each having a substantially U-shaped cross-section.

8. An angle bracket as defined in claim 7 wherein said U-shaped cross section is defined by each leg having first and second upstanding sidewalls extending normally from a base.

9. An angle bracket as defined in claim 8 wherein each leg further includes:

first and second flanges respectively extending normally from the first and second upstanding sidewalls.

10. An angle bracket as defined in claim 9 wherein said first and second flanges extend inward toward each other.

11. An angle bracket as defined in claim 9 wherein said first and second flanges extend outward away from each other.

12. An angle bracket as claimed in claim 7 further comprising:
strengthening means for strengthening an interconnection between said second and third legs.

13. An angle bracket as claimed in claim 12 wherein said strengthening means includes at least one tab extending from said third leg and at least one slot within the second leg for receiving said tab.

14. An angle bracket as claimed in claim 12 wherein said strengthening means includes at least one tab extending from the second leg and at least one slot within the third leg for receiving said tab.

15. An angle bracket as defined in claim 7 wherein each leg has a width and wherein the angle bracket further includes:
a base extending substantially across the width of each leg, the base having first and second sides; and
upstanding sidewalls extending from the first and second sides of the base along each leg to form the substantially U-shaped cross-section.

16. An angle bracket as defined in claim 7 wherein the first leg has a tab and the third leg has a slot, the tab being interlocked with the slot to interconnect the first and third legs.

17. An angle bracket comprising:
a single piece substantially planar elongated metal blank, the blank having first and second ends oppositely disposed about a length of the blank, the blank further having a plurality of separately spaced transverse fold lines disposed along the length of the blank;
the metal blank forming a substantially triangular shape comprised of first, second and third legs, the second leg intersecting with the first and third legs at locations along the metal blank defined by transverse fold lines;
the metal blank further having means for defining an interconnection between the first and second ends such that the blank maintains its substantially triangular shape;
the blank including a plurality of longitudinal fold lines extending substantially along the length of the blank;
the bracket having a plurality of upstanding sidewalls extending from a base of each leg such that the blank forms a substantially U-shaped cross-section, the sidewalls extending from the base of each leg at locations defined by at least some of said longitudinal fold lines.

18. An angle bracket as claimed in claim 17 having a plurality of flanges extending from said plurality of upstanding sidewalls, the plurality of flanges comprising coplanar first and second flanges extending along each leg, the plurality of flanges extending from the plurality of upstanding sidewalls at locations defined by additional longitudinal fold lines.

19. An angle bracket as claimed in claim 18 wherein the plurality of first and second flanges face inward toward each other.

20. An angle bracket as claimed in claim 18 wherein the plurality of first and second flanges face outward away from each other.

21. An angle bracket as claimed in claim 17 wherein the plurality of upstanding sidewalls extend upward from a first surface of the base along the first and third legs and extend downward from a second surface of the base along the second leg.

22. An angle bracket as claimed in claim 17 further comprising:
strengthening means for strengthening an interconnection between said first and second legs.

23. An angle bracket as defined in claim 17 wherein each leg has a width and wherein the base has first and second sides, the base of each leg extending substantially across the width of its corresponding leg, the upstanding sidewalls extending from the first and second sides of the base along each leg.

24. An angle bracket comprising:
a substantially planar elongated metal blank, the blank having at least one transverse fold line disposed along the length of the blank;
the bracket including first, second and third legs, at least the first and second legs being formed from the metal blank and intersecting at a location along the metal blank defined by the transverse fold line;
the bracket further including means for defining an interconnection between the first and third legs such that the first, second and third legs form a substantially triangular shape;
the bracket further including strengthening means for strengthening the intersection between said first and second legs.

25. An angle bracket formed from a single piece metal blank, the angle bracket comprising:
first, second and third legs, the first leg being contiguous and interconnecting with the second leg, the second leg being contiguous and interconnecting with the third leg, said legs being positioned to define a substantially triangular bracket;
means for defining an interconnection between said first and third legs; and
strengthening means for strengthening the interconnection between said first and second legs.

26. An angle bracket as claimed in claim 25 including means for strengthening the interconnection between said second and third legs.

27. An angle bracket as claimed in claim 25 wherein said strengthening means includes at least one tab extending from said first leg and at least one slot within the second leg for receiving said tab.

28. An angle bracket as claimed in claim 25 wherein said strengthening means includes at least one tab extending from said second leg and at least one slot within the first leg for receiving said tab.

29. An angle bracket as claimed in claim 25 wherein the means for defining an interconnection between said first and third legs includes:
means for defining a first slot in the third leg;
a locking tab extending from the first leg, the locking tab being interlocked with the first slot to interconnect the first and third legs;
means for defining a second slot in the third leg;
an alignment tab extending from the first leg, the alignment tab fitting within the second slot.

30. An angle bracket comprising:
a single-piece metal blank, having first and second transverse fold lines, the metal blank being folded along the first and second transverse fold lines to form a horizontal leg, a vertical leg and a cross leg, the cross leg and the horizontal leg intersecting at the first transverse fold line, the horizontal leg and the vertical leg intersecting at the second transverse fold line, the legs being folded to define a substantially triangular bracket;

the cross leg having a tab and the vertical leg having a slot, the tab being interlocked with the slot to interconnect the cross and vertical legs.

31. A single-piece metal blank for forming an angle bracket, the metal blank comprising:

first and second ends oppositely disposed about a length of the blank;

first and second longitudinal fold lines extending along the length of the blank;

a center segment extending along the length of the blank and between the first and second longitudinal fold lines;

first and second outer segments extending along the length of the blank, the first and second outer segments being disposed on opposing sides of the center segment;

first and second transverse fold lines spaced apart along the length of the blank, each transverse fold line extending across the center segment; and first, second and third legs, the first leg extending from the first end to the first transverse fold line, the second leg extending from the first transverse fold line to the second transverse fold line, the third leg extending from the second transverse fold line to the second end, the first leg being contiguous with the second leg only along the center segment, the second leg being contiguous with the third leg only along the center segment.

32. A metal blank as defined in claim 31 wherein:

the third leg has a locking slot, and wherein the metal blank includes a locking tab extending from the first leg, the locking tab and locking slot being constructed and arranged so that the locking tab can be interlocked with the locking slot when the blank is folded into an angle bracket.

33. A metal blank as defined in claim 32 wherein:

the first leg has an alignment tab extending therefrom and the second leg has an alignment slot formed therein, the alignment tab and alignment slot each being constructed and arranged so that the alignment tab can fit within the alignment slot when the blank is folded into an angle bracket.

34. A metal blank as defined in claim 32 wherein:

the third leg has an alignment tab extending therefrom and the second leg has an alignment slot formed therein, the alignment tab and alignment slot each being constructed and arranged so that the alignment tab can fit within the alignment slot when the blank is folded into an angle bracket.

35. A metal blank as defined in claim 32 wherein:

the second leg has an alignment tab extending therefrom and the third leg has an alignment slot formed therein, the alignment tab and alignment slot each being constructed and arranges so that the alignment tab can fit within the alignment slot when the blank is folded into an angle bracket.

36. A metal blank as defined in claim 32 wherein:

the second leg has an alignment tab extending therefrom and the first leg has an alignment slot formed therein, the alignment tab and alignment slot each being constructed and arranged so that the alignment tab can fit within the alignment slot when the blank is folded into an angle bracket.

37. A metal blank as defined in claim 32 wherein:

the first leg has a first alignment tab extending therefrom and the second leg has a first alignment slot formed therein, the first alignment tab and first alignment slot being constructed and arranged so that the first alignment tab can fit within the first alignment slot when the blank is folded into an angle bracket; and the third leg has a second alignment tab extending therefrom and the second leg has a second alignment slot formed therein, the second alignment tab and second alignment slot being constructed and arranged so that the second alignment tab can fit within the second alignment slot when the blank is folded into an angle bracket.

38. A metal blank as defined in claim 32 wherein:

the second leg has a first alignment tab extending therefrom and the first leg has a first alignment slot formed therein, the first alignment tab and first alignment slot being constructed and arranged so that the first alignment tab can fit within the first alignment slot when the blank is folded into an angle bracket; and the second leg has a second alignment tab extending therefrom and the third leg has a second alignment slot formed therein, the second alignment tab and second alignment slot being constructed and arranged so that the second alignment tab can fit within the second alignment slot when the blank is folded into an angle bracket.

39. An angle bracket comprising:

a single piece substantially planar elongated metal blank, the blank having first and second ends oppositely disposed about a length of the blank, the blank further having a plurality of separately spaced transverse fold lines disposed along the length of the blank;

the metal blank forming a substantially triangular shape comprised of first, second and third legs, the second leg intersecting with the first and third legs at location along the metal blank defined by transverse fold lines;

the metal blank further having means for defining an interconnection between the first and second legs such that the blank maintains its substantially triangular shape;

the second leg having means for receiving a support member and for supporting the support member in a substantially horizontal position.

40. An angle bracket comprising:

a single piece substantially planar elongated metal blank, the blank having first and second ends oppositely disposed about a length of the blank, the blank further having a plurality of separately spaced transverse fold lines disposed along the length of the blank;

the metal blank forming a substantially triangular shape comprised of first, second and third legs, the second leg intersecting with the first and third legs at locations along the metal blank defined by transverse fold lines, the first and second ends being interconnected so that the blank maintains its substantially triangular shape;

the first leg having a tab and the second leg having a slot, the tab and slot being constructed and arranged so that the metal forming each is in compression.

41. An angle bracket as defined in claim 40 wherein the third leg has a second tab and the second leg has a second slot, the second tab and second slot being constructed and arranged so that the metal forming each is in compression.

42. An angle bracket comprising:
a single piece substantially planar elongated metal blank, the blank having first and second ends oppositely disposed about a length of the blank, the blank further having a plurality of separately spaced transverse fold lines disposed along the length of the blank;

the metal blank forming a substantially triangular shape comprised of first, second and third legs, the second leg intersecting with the first and third legs at locations along the metal blank defined by transverse fold lines, the first and second ends being interconnected so that the blank maintains its substantially triangular shape;

the second leg having a tab and the first leg having a slot, the tab and slot being constructed and arranged so that the metal forming each is in compression.

43. An angle bracket as defined in claim 42 wherein the second leg has a second tab and the third leg has second slot, the second tab and second slot being constructed and arranged so that the metal forming each is in compression.

* * * * *